(12) United States Patent
Doyle et al.

(10) Patent No.: US 10,716,827 B2
(45) Date of Patent: *Jul. 21, 2020

(54) COMPOSITIONS AND METHODS FOR ENHANCING PEPTIDE STABILITY AGAINST PROTEASE DIGESTION

(71) Applicants: Syracuse University, Syracuse, NY (US); Xeragenx LLC, St. Louis, MO (US)

(72) Inventors: Robert Doyle, Manlius, NY (US); Jonathan D. Bortz, St. Louis, MO (US); David S. Hermelin, St. Louis, MO (US)

(73) Assignee: Syracuse University, Syracuse, NY (US)

( * ) Notice: Subject to any disclaimer, the term of this patent is extended or adjusted under 35 U.S.C. 154(b) by 25 days.

This patent is subject to a terminal disclaimer.

(21) Appl. No.: 15/575,501

(22) PCT Filed: May 20, 2016

(86) PCT No.: PCT/US2016/033461
§ 371 (c)(1),
(2) Date: Nov. 20, 2017

(87) PCT Pub. No.: WO2016/187512
PCT Pub. Date: Nov. 24, 2016

(65) Prior Publication Data
US 2018/0140669 A1     May 24, 2018

Related U.S. Application Data

(60) Provisional application No. 62/169,233, filed on Jun. 1, 2015, provisional application No. 62/164,808, filed on May 21, 2015, provisional application No. 62/164,045, filed on May 20, 2015.

(51) Int. Cl.
*A61K 38/00*     (2006.01)
*A61K 38/17*     (2006.01)
*A61K 47/55*     (2017.01)

(52) U.S. Cl.
CPC ........ *A61K 38/1709* (2013.01); *A61K 47/551* (2017.08)

(58) Field of Classification Search
None
See application file for complete search history.

(56) References Cited

FOREIGN PATENT DOCUMENTS

| WO | 1996/04016 | 2/1996 |
|----|------------|--------|
| WO | 2008/109068 | 9/2008 |

OTHER PUBLICATIONS

Clardy-James et al, Site-Selective Oxidation of Vitamin B12 Using 2-Iodoxybenzoic Acid, SYNLETT, 2012, 23, pp. 2363-2366, (Year: 2012).*
Fedosov S,N. "Human intrinsic factor expressed in the plant *Arabidopsis thaliana*," Eur J Biochem. Aug. 2003;270(16):3362-7 (Year: 2003).*
Alsenz J et al: "Oral absorption of peptides through the cobalamin (vitamin B12) pathway in the rat intestine", Pharmaceutical Research 2000 US, vol. 17, No. 7, 2000, pp. 825-832, XP55295840, ISSN: 0724-8741 abstract, p. 826, sections "Binding of Cbl-DP3, Cbl-Hex-DP3 and of Cbl-LHRH to CBL-Binding Proteins", "Association of IF-[57Co]-Cbl, IF-Cbl-[125I]-DP3, IF-Cbl-HEX-[125I]-DP3 or IF-Cbl-[125I]-LHRH with Caco-2 Monolayers and Transcytosis of Complexes" p. 831, left column, first paragraph.
Ron L. Bonaccorso, et al., "Enhanced Peptide Stability Against Protease Digestion Induced by Intrinsic Factor Binding of a Vitamin B 12 Conjugate of Exendin-4", Molecular Pharmaceutics, vol. 12, No. 9, Sep. 8, 2015 (Sep. 8, 2015), pp. 3502-3506, XP055295838, US ISSN: 1543-8384, DOI: 10.1021/acs.molpharmaceut.5b00390 the whole document.
Ronald Bonaccorso et al: "Synthesis, characterization, and pharmacodynamics of vitamin B12 conjugated exendin 4", Abstracts of Papers American Chemical Society, Sep. 8, 2013 (Sep. 8, 2013), XP055295868, Retrieved from the Internet: URL:http://acselb-529643017.us-west-2.elb.amazonaws.com/chem/246nm/program/view.php [retrieved on Aug. 17, 2016] abstract.
International Search Report Form PCT/ISA/220, International Application No. PCT/US2016/033461, pp. 1-14, dated Aug. 26, 2016.

* cited by examiner

*Primary Examiner* — Thomas S Heard
(74) *Attorney, Agent, or Firm* — Bond Schoeneck & King, PLLC; David Nocilly; George McGuire (57) ABSTRACT

The present invention relates to the digestion of peptides by pancreatic proteases and, more specifically, to compositions and methods for protecting against protease digestion.

16 Claims, 7 Drawing Sheets
Specification includes a Sequence Listing.

COMPOSITIONS AND METHODS FOR ENHANCING PEPTIDE STABILITY AGAINST PROTEASE DIGESTION

FIELD OF THE INVENTION

The present invention relates to protecting peptides from protease digestion, and in specific embodiments, to compositions and methods for protecting against pancreatic protease digestion.

BACKGROUND OF THE INVENTION

A wide variety of peptide drugs are now produced on a commercial scale as a result of advances in the biotechnology field. Most of these therapeutic peptides are still administered by the parenteral route because of insufficient absorption from the gastrointestinal tract. Peptide drugs are usually indicated for chronic conditions, and the use of injections on a daily basis during long-term treatment has obvious drawbacks. In contrast to this inconvenient and potentially problematic method of drug administration, the oral route offers the advantages of self-administration with a high degree of patient acceptability and compliance. The main reasons for the low oral bioavailability of peptide drugs are pre-systemic enzymatic degradation and poor penetration of the intestinal mucosa. A considerable amount of research has focused on overcoming the challenges presented by these intestinal absorption barriers to provide effective oral delivery of peptide and protein drugs. Attempts to improve the oral bioavailability of peptide drugs have ranged from changing the physicochemical properties of peptide molecules to the inclusion of functional excipients in specially adapted drug delivery systems. However, the progress in developing an effective peptide delivery system has been hampered by factors such as the inherent toxicities of absorption-enhancing excipients, variation in absorption between individuals, and potentially high manufacturing costs.

Thus, there is a need in the art for a method to deliver peptide drugs that decreases proteolytic degradation while enhancing gastrointestinal absorption without toxic side effects thereby overcoming the barriers associated with peptide drug delivery and absorption.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION OF THE INVENTION

The present invention comprises the use of intrinsic factor to protect a peptide from protease degradation. A peptide of interest is conjugated to $B_{12}$ and the $B_{12}$ conjugate is then complexed with intrinsic factor. Such a composition is suitable for administration as it protects the peptide from protease degradation. Specifically, the composition may be suitable for oral administration. Accordingly, the invention provides a method to deliver peptide drugs that decreases proteolytic degradation while enhancing gastrointestinal absorption without toxic side effects thereby overcoming the barriers previously associated with peptide drug delivery and absorption.

I. Composition

The present invention encompasses a pharmaceutical composition comprising intrinsic factor and $B_{12}$ or an analog thereof, wherein the $B_{12}$ or analog thereof is conjugated to a peptide. $B_{12}$ analogs may be modified to improve conjugation chemistry, bioavailability, solubility, stability, handling properties, or a combination thereof, as compared to an unmodified version of $B_{12}$. Thus, in another aspect, a composition of the invention comprises a modified $B_{12}$ or $B_{12}$ analog. In still another aspect, a composition of the invention comprises a prodrug of $B_{12}$ or a $B_{12}$ analog.

A composition of the invention may further comprise a pharmaceutically acceptable excipient, carrier or diluent. Further, a composition of the invention may contain preserving agents, solubilizing agents, stabilizing agents, salts (substances of the present invention may themselves be provided in the form of a pharmaceutically acceptable salt), buffers, or antioxidants.

(a) Vitamin $B_{12}$ (Cobalamin)

Vitamin $B_{12}$ is a water-soluble vitamin with a highly complex structure, comprising a midplanar corrin ring composed of four pyrroline elements linked to a central cobalt (III) atom. Throughout the disclosure vitamin $B_{12}$, $B_{12}$ and cobalamin may be used interchangeably.

Figure 1:
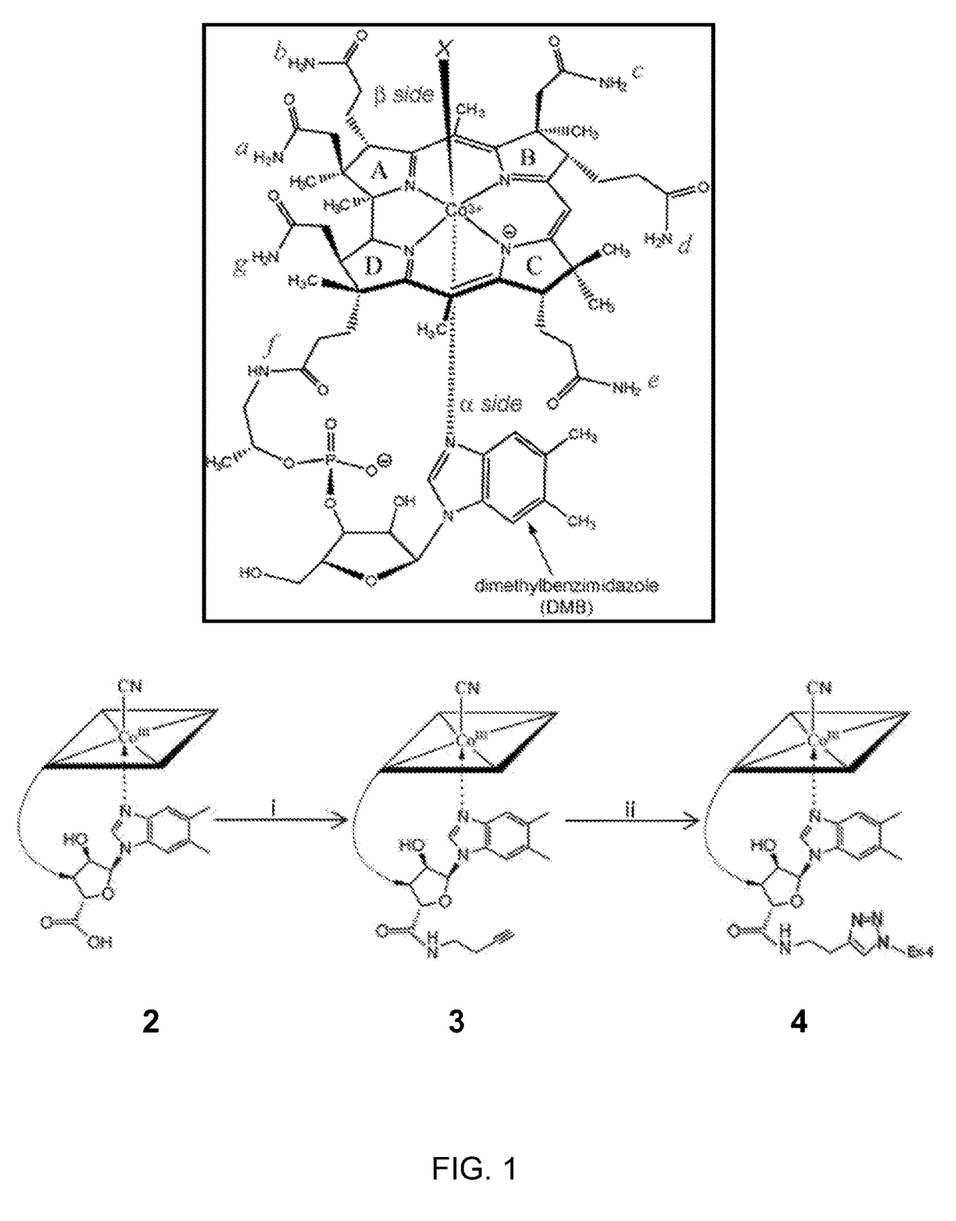
FIG. 1 depicts the structure of Vitamin $B_{12}$ showing the Co (III) atom coordinated by the four nitrogens of the corrin ring, dimethylbenzimidazole (DMB), and the X group which can be a cyanide, methyl, or deoxyadenosyl groups and a diagram showing the synthesis of a $B_{12}$-Ex-4 conjugate (compound 4).

In the structure of vitamin $B_{12}$, the central cobalt (III) atom is six-coordinated, with the equatorial positions filled by the nitrogen atoms of the corrin macrocycle. The (conventionally) 'lower', 'α'-axial site is occupied by an imidazole nitrogen atom from a 5',6'-dimethylbenzimidazole (DMB) base whereas the 'upper', β-axial site can be occupied by various X groups (e.g. $CN^-$, $CH_3^-$, $Ado^-$, $SCN^-$, $SeCN^-$, $SO_3^-$ and thiourea). The corrin ring incorporates seven amide side chains, three acetamides (a, c, g) and four propionamides (b, d, e, f). The four pyrrole rings are usually indicated as A, B, C and D, as shown in FIG. 1.

Several functional groups are readily available for modification and/or conjugation on $B_{12}$, including propionamides, acetamides, hydroxyl groups, the cobalt (III) ion and the phosphate moiety. As used herein, a modification of $B_{12}$ may be any modification on $B_{12}$ that improves conjugation chemistry, bioavailability, solubility, stability, handling properties, or a combination thereof. As used herein, conjugation of $B_{12}$ describes the conjugation of a peptide to $B_{12}$ or modified $B_{12}$. Accordingly, a $B_{12}$ conjugate of the invention may be modified and/or conjugated at a propionamide, acetamide, hydroxyl group, the cobalt (III) ion and the phosphate moiety, provided the $B_{12}$ conjugate binds IF. Non-limiting examples of modification or conjugation sites for a $B_{12}$ conjugate of the invention include at the a-position or b-position on the A-ring, at the c-position or d-position on the B-ring, at the e-position on the C-ring, at the g-position on the D ring, at the f-position, at the phosphate moiety, at the 5'- or 2'-hydroxyl on the ribose, and at the cobalt ion. Preferred sites of modification and/or conjugation may include sites on the A ring such as the b-position, sites on the C ring such as the e-position, sites on the ribose unit such as the 5'-hydroxyl group, and the cobalt cation. Specifically, the e-position may be modified and/or conjugated to allow interaction with IF. However, other sites of modification and/or conjugation may be utilized provided they maintain the binding affinity of $B_{12}$ for IF. In a specific embodiment, the 5'-hydroxyl on the ribose may be modified to a carboxylic acid. The resulting carboxylic acid may then be used to conjugate $B_{12}$ to a peptide. A method of performing this is described in more detail below and in the Examples.

Methods for modification and/or conjugation to $B_{12}$ are known in the art. The following provides non-limiting examples of methods for modification and/or conjugation. It is contemplated that various other methods for modification and/or conjugation common in the art of synthetic chemistry may be used. For example, carefully controlled partial hydrolysis of cyanocobalamin under acidic conditions gives access to desirable b and e acids. Methods for 5'-OH functionalization may rely on the reaction of cyanocobalamin ((CN)Cbl) with anhydrides, furnishing unstable ethers. Another method for conjugation may be the carbamate or carbonate methodology as described by Russell-Jones (WO 1999/065390, which is hereby incorporated by reference in its entirety). Briefly, the hydroxyl group at position 5' is first reacted with a carbonyl group equivalent—1,1'-carbonyldiimidazole (CDI) or 1,1'-carbonylbis(1,2,4-triazole) (CDT)—and then treated with an amine or an alcohol giving carbamates and carbonates, respectively, at the 5'-position of the ribose tail. Alternatively, the 5'-OH group can be oxidized to the corresponding carboxylic acid using the 2-iodoxybenzoic acid (IBX)/2-hydroxypyridine (HYP) system as an oxidant and then coupled with amines. Another effective approach may rely on [1,3] dipolar cycloaddition. The 5'-OH is transformed into a good leaving group and subsequently substituted with an azide. The resulting "clickable" azide is stable and highly active in the copper-catalyzed as well as in the strain promoted [1,3] dipolar cycloaddition (CuAAC or SPAAC) to alkynes. This methodology is described in detail in Chrominski et al, *Chem Eur J* 2013; 19: 5141-5148, which is hereby incorporated by reference in its entirety. In a specific embodiment, the 5'-OH is oxidized to a carboxylic acid. An alkyne is then added to the carboxylic acid. A peptide may then be conjugated to $B_{12}$ via the alkyne group.

Functionalization of the cobalt ion may be accomplished by either alkylation or utilization of cyanide ligand properties to act as an electron pair donor for transition metals, resulting in bimetallic complexes. The synthesis of organometallic species requires reduction of the cobalt (III) to cobalt (I) $B_{12}$ and its subsequent reaction with electrophiles: alkyl halides, acyl halides, Michael acceptors, epoxides, etc. Alternatively, reduction may not be required and instead, the direct reaction of (CN)Cbl with terminal alkynes in the presence of Cu(I) salts may furnish acetylides in excellent yields. This methodology may allow the conjugation of two moieties to $B_{12}$ and is described in further detail in Chrominski et al, *J Org Chem* 2014; 79: 7532-7542, which is hereby incorporated by reference in its entirety. Accordingly, it is contemplated that two peptides may be conjugated to $B_{12}$. Briefly, using this methodology, "doubly clickable" vitamin $B_{12}$, a valuable building block for further functionalization via [1, 3] dipolar azide-alkyne cycloaddition, may be prepared. A combination of AAC (CuAAC and SPAAC) with the carbamate method may allow conjugation at both the central cobalt ion and the 5'-position.

$B_{12}$ or an analog thereof and a peptide may be: i) conjugated directly together; or ii) held apart by a 'linker' to produce distance between the $B_{12}$ or an analog thereof and the peptide. The peptide is described in more detail in Section I (b). In an embodiment, $B_{12}$ or an analog thereof may be conjugated to a peptide directly. In another embodiment, an intervening amino acid sequence or linker may be used to conjugate the peptide to $B_{12}$. It is to be understood that conjugation of the $B_{12}$ or an analog thereof to a peptide will not adversely affect either the binding function of the $B_{12}$ or an analog thereof to IF or the function of the peptide. Suitable linkers include, but are not limited to, amino acid chains and alkyl chains functionalized with reactive groups for conjugating to both the $B_{12}$ or analog thereof and the peptide.

In an embodiment, the linker may include amino acid side chains, referred to as a peptide linker. Accordingly, amino acid residues may be added to $B_{12}$ or an analog thereof for the purpose of providing a linker by which $B_{12}$ or an analog thereof can be conveniently affixed to a peptide. Amino acid residue linkers are usually at least one residue and can be 40 or more residues, more often 1 to 10 residues. Typical amino acid residues used for linking are tyrosine, cysteine, lysine, glutamic and aspartic acid, or the like.

In another embodiment, the linker may be an alkyl chain linking group. For example, by reacting an amino group of $B_{12}$ or an analog thereof with a first functional group on the alkyl chain, such as a carboxyl group or an activated ester. Subsequently a peptide may be attached to the alkyl chain to complete the formation of a conjugate by reacting a second functional group on the alkyl chain with an appropriate group on the peptide. The second functional group on the alkyl chain is selected from substituents that are reactive with a functional group on the peptide while not being reactive with $B_{12}$ or an analog thereof. For example, when the peptide incorporates a functional group, such as a carboxyl group or an activated ester, the second functional group of the alkyl chain linking group can be an amino group. Alternatively, by reacting a carboxylic acid group generated from the oxidation of the 5'-hydroxyl of the ribose on $B_{12}$, with a bifunctional amine-alkyne of variable methylene spacer length, a $B_{12}$-alkyne compound may be generated. Subsequently, a peptide may be attached to the alkyl chain to complete the formation of the conjugate by reaction a second functional group on the alkyl chain with an appropriate group on the peptide. In the aforementioned embodiment, the second functional group on the alkyl chain is an alkyne. A peptide modified with a functional group that reacts with an alkyne may then be conjugated to the alkyl chain. For example, a peptide modified with an azido group may be conjugated to the alkyne group on the alkyl chain.

It will be appreciated that formation of the conjugate may require protection and deprotection of the functional groups present in order to avoid formation of undesired products. Protection and deprotection are accomplished using protecting groups, reagents, and protocols common in the art of organic synthesis. It will be appreciated that linking groups may alternatively be coupled first to the peptide and then to $B_{12}$ or an analog thereof. An alkyl chain linking group may be one to 40 or more atoms long, more often 1 to 10 atoms long. Additionally, an alkyl chain linking group may comprise one or more heteroatoms (e.g. O, N, S). In certain embodiment, an alkyl chain linking group may be 1, 2, 3, 4, 5, 6 or 7 atoms long. In a specific embodiment, an alkyl chain linking group may comprise 3, 4, 5, or 6 carbons. In another specific embodiment, an alkyl chain linking group may comprise 4 carbons.

An alternative chemical linking group to an alkyl chain is polyethylene glycol (PEG), which is functionalized in the same manner as the alkyl chain described above for incorporation in the conjugates. $B_{12}$ or an analog thereof may be PEGylated for improved systemic half-life and reduced dosage frequency. In an embodiment, PEG may be added to a linker. As such, $B_{12}$ or an analog thereof may comprise a linker and PEG.

(b) Peptide

In an aspect, $B_{12}$ or an analog thereof may be conjugated to a peptide. By "peptide" is meant an amino acid sequence that includes 5 or more amino acid residues. "Peptide" refers to both short chains, commonly referred to as peptides, oligopeptides, or oligomers, and to longer chains, up to about 100 residues in length. A peptide may comprise about 5 or more amino acids. For example, a peptide may comprise about 5 or more, about 10 or more, about 15 or more, about 20 or more, about 25 or more, about 30 or more, about 35 or more, about 40 or more, about 45 or more, about 50 or more, about 55 or more, about 60 or more, about 65 or more, about 70 or more, about 75 or more, about 80 or more, about 85 or more, about 90 or more, about 95 or more, or about 100 or more amino acids. In certain embodiments, a peptide may comprise 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 amino acids. In other embodiments, a peptide may comprise from about 30 to about 60 amino acids. In still other embodiments, a peptide may comprise from about 35 to about 55 amino acids. In yet other embodiments, a peptide may comprise from about 40 to about 55 amino acids. In a specific embodiment, a peptide may comprise about 45 amino acids. In an exemplary embodiment, a peptide comprises 45 amino acids.

A peptide may be ordered (α-helix or β-sheet), disordered, or a combination thereof. In certain embodiments, a peptide may adopt an α-helical structure. In other embodiments, a peptide may adopt an α-helical structure with a disordered terminal end.

A peptide may be a peptide known in the art to be prone to protease degradation. For example, a peptide may be a peptide known in the art to be prone to degradation by proteases found in the gastrointestinal tract. In a specific embodiment, the proteases may be pancreatic proteases. In certain embodiments, a peptide may be an Exendin-4 (EX-4) peptide. An EX-4 peptide has potential for treatment of type II diabetes and is homologous to glucagon-like peptide-1 (GLP-1). In general, an EX-4 peptide interacts with GLP-1R. In certain embodiments, the N-terminal part of an EX-4 peptide interacts with GLP-1R core domain and the helical part of an EX-4 peptide interacts with the extracellular domain of GLP-1R. In a specific embodiment, a peptide may comprise the sequence set forth in SEQ ID NO: 2 (HGEGTFTSDLSKQMEEEAVRLFIENWLKNGGPSSGAPSS-GAPPPS). Alternatively, a peptide of the invention may be modified to facilitate conjugation to $B_{12}$. For example, a peptide may comprise the sequence set forth in SEQ ID NO: 1 (HGEGTFTSDLS(Kazido)QMEEEAVRLFIENWLKNG-GPSSGAPSSGAPPPS), wherein the lysine at the 12 position is modified with an azido group.

A peptide of the invention may be subject to various changes, substitutions, insertions, and deletions where such changes provide for certain advantages in its use. Thus, the invention encompasses any of a variety of forms of peptide derivatives that include amides, cyclized peptides, polymerized peptides, conservatively substituted variants, analogs, fragments, peptoids, chemically modified peptides, and peptide mimetics. In addition, a peptide can be modified by terminal-$NH_2$ acylation (e.g., acetylation, or thioglycolic acid amidation) or by terminal-carboxylamidation (e.g., with ammonia, methylamine, and the like terminal modifications).

Peptides of the invention may comprise naturally occurring amino acids, synthetic amino acids, genetically encoded amino acids, non-genetically encoded amino acids, and combinations thereof. Peptides may include both L-form and D-form amino acids.

Representative non-genetically encoded amino acids may include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids may include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence similar to a sequence of a reference peptide in which one or more residues have been conservatively substituted with a functionally similar residue and which displays the same or similar targeting activity. The phrase "conservatively substituted variant" also includes peptides wherein a residue is replaced with a chemically derivatized residue, provided that the resulting peptide displays targeting activity.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the present invention, including peptoids, may be synthesized by any of the techniques that are known to those skilled in the art of peptide synthesis. Synthetic chemistry techniques, such as a solid-phase Merrifield-type synthesis, may be preferred for reasons of purity, antigenic specificity, freedom from undesired side products, ease of production and the like. A summary of representative techniques can be found in Stewart & Young (1969) Solid Phase Peptide Synthesis. Freeman, San Francisco; Merrifield (1969) Adv Enzymol Relat Areas Mol Biol 32:221-296; Fields & Noble (1990) Int J Pept Protein Res 35:161-214; and Bodanszky (1993) Principles of Peptide Synthesis. 2nd rev. ed. Springer-Verlag, Berlin; New York. Solid phase synthesis techniques can be found in Andersson et al. (2000) Biopolymers 55:227-250, references cited therein, and in U.S. Pat. Nos. 6,015,561, 6,015,881, 6,031,071, and 4,244,946. Peptide synthesis in solution is described by Schröder & Lübke (1965) The Peptides. Academic Press, New York. Appropriate protective groups usable in such synthesis are described in the above texts and in McOmie (1973) Protective Groups in Organic Chemistry. Plenum Press, London, New York. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif. and PeptidoGenics of Livermore, Calif.).

(c) Intrinsic Factor

In an aspect, IF is bound to a $B_{12}$ conjugate of the invention thereby forming a complex. As used herein, a complex of the invention comprises IF complexed to a $B_{12}$ conjugate of the invention. Intrinsic factor (IF) is a glycosylated protein that is secreted from the gastric mucosa and the pancreas. IF binds $B_{12}$ with picomolar affinity ($K_d \sim 1$ pM). In the $B_{12}$ uptake pathway, the IF protein facilitates transport of $B_{12}$ across the intestinal enterocyte, which occurs by receptor-mediated endocytosis at the apically expressed IF-$B_{12}$ receptor (cubilin). Cubilin works to transport $B_{12}$ in concert with an anchoring protein amnionless (Am). Following transcytosis, and between 2.5 and 4 h after initial ingestion, $B_{12}$ appears in blood plasma bound to the third trafficking protein, transcobalamin II (TCII). The inventors have discovered that conjugating a peptide to $B_{12}$ which is then complexed with IF, mitigates cleavage of the peptide in the presence of proteases. Such a complex provides for oral administration of protease labile peptides to the gastrointestinal tract thereby enhancing their bioavailability by avoiding protease cleavage. In a specific embodiment, the proteases may be pancreatic proteases.

The IF may be complexed to $B_{12}$ before or after conjugation of $B_{12}$ or an analog thereof to a peptide. In a specific embodiment, IF may be complexed to $B_{12}$ or an analog thereof after conjugation of $B_{12}$ or an analog thereof to a peptide. In an embodiment, IF may be pre-complexed to a $B_{12}$ conjugate by combining the conjugate with IF in solution. By way of non-limiting example, $B_{12}$ conjugate may be combined with IF in PBS at pH 7.4 or in MES buffer at pH 5.5 or in water at pH 8 at temperatures ranging from about 25° C. to about 37° C. For binding, IF may be contacted with $B_{12}$ conjugate for at least 30 minutes. Alternatively, IF may be contacted with $B_{12}$ conjugate for at least 5 min, at least 10 min, at least 15 minutes, at least 20 minutes, at least 30 minutes, at least 45 minutes, at least 1 hour, at least 2 hours, at least 3 hours, at least 4 hours, at least 5 hours or at least 6 hours. A skilled artisan would be able to determine the various conditions upon which IF and $B_{12}$ conjugate may be pre-complexed.

For pre-complexing of IF and the $B_{12}$ conjugate, IF and the $B_{12}$ conjugate may be combined in solution. One IF complexes with one $B_{12}$ conjugate. Accordingly, the ratio of IF to $B_{12}$ conjugate added to solution may be 1:1. However, to facilitate saturation of the IF with $B_{12}$ conjugate, a greater amount of IF may be added to solution relative to $B_{12}$ conjugate. For example, the ratio of IF to $B_{12}$ conjugate may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, or 100:1. In specific embodiments, the ratio of IF to $B_{12}$ conjugate may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, or 10:1. In other embodiments, an excess of 5% or more IF relative to $B_{12}$ conjugate may be added to solution. For example, an excess of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 70%, 80%, 90% or 100% IF relative to $B_{12}$ conjugate may be added to solution. In specific embodiments, an excess of 5%, 6%, 7%, 8%, 9%, 10%, 11%, 12%, 13%, 14%, or 15% IF relative to $B_{12}$ conjugate may be added to solution. Preferably, in some embodiments, excess IF is added to the solution relative to $B_{12}$ conjugate. However, it may be necessary to add a greater amount of $B_{12}$ conjugate relative to IF to reduce or eliminate un-complexed IF. Accordingly, the ratio of $B_{12}$ conjugate to IF may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, or 100:1. In specific embodiments, the ratio of $B_{12}$ conjugate to IF may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, or 10:1. In other embodiments, an excess of 5% or more $B_{12}$ conjugate relative to IF may be added to solution. For example, an excess of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 70%, 80%, 90% or 100% $B_{12}$ conjugate relative to IF may be added to a solution. In a specific embodiment, an excess of 5%, 6%, 7%, 8%, 9%, 10%, 11%, 12%, 13%, 14%, or 15% $B_{12}$ conjugate relative to IF may be added to a solution. Prior to administration of a composition of the invention, it may be necessary to remove un-complexed IF and/or un-complexed $B_{12}$ conjugate.

IF of the invention may be expressed and purified via standard methodology. In a preferred embodiment, IF of the invention is in a pharmaceutically acceptable form. As used in this context, "pharmaceutically acceptable" means the IF is expressed in an environment that is not contaminated with other $B_{12}$ binding proteins or B12 analogs, is extracted in an environment that is not contaminated with other $B_{12}$ binding proteins, and is scalable and reproducible per applicable regulatory standards. IF may be expressed and purified from a transgenic plant, such as *Arabidopsis*. For example, see US 2010/0184642, which is hereby incorporated by reference in its entirety. The expressed and purified IF may be from any species, provided it binds to $B_{12}$ and human cubilin. A skilled artisan will appreciate that IF can be found in a variety of species. Non-limiting examples include human (NP_005133.2), mouse (P52787.2), rat (NP_058858.1), dog (Q5XWD5.1), cat (XP_003993466.1), cattle (NP_001193168.1), non-human primates (EHH56203.1, XP_004051305.1), and horse (XP_008508117.1). It is appreciated that the present invention is directed to homologs of IF in other organisms and is not limited to the human protein. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. In some embodiments, a homolog has at least 80%, at least 81%, at least 82%, at least 83%, at least 84%, at least 85%, at least 86%, at least 87%, at least 88%, or 89% identity to human IF. In another embodiment %, a homolog has at least 90%, at least 91 at least %, at least 92 at least %, at least 93 at least %, at least 94%, at least 95%, at least 96%, at least 97%, at least 98%, at least 99%, or at least 100% identity to human IF. For instance, a homolog may have at least 80%, at least 81%, at least 82%, at least 83%, at least 84%, at least 85%, at least 86%, at least 87%, at least 88%, or 89% identity to human IF. In another embodiment %, a homolog has at least 90%, at least 91 at least %, at least 92 at least %, at least 93 at least %, at least 94%, at least 95%, at least 96%, at least 97%, at least 98%, at least 99%, or at least 100% identity to the IF sequence accession number NP_005133.2.

In a specific embodiment, the IF comprises the sequence disclosed in accession number NP_005133.2. In other embodiments, the IF comprises the sequence disclosed in accession number NP_005133.2 but for one to 10 conservative amino acid substitutions. For example, the IF comprises the sequence disclosed in accession number NP_005133.2 but for 1, 2, 3, 4, 5, 6, 7, 8, 9 or 10 conservative amino acid substitutions. As used herein, a "conservative amino acid substitution" is one in which the amino acid residue is replaces with an amino acid residue having a similar side chain. Families of amino acid residues having similar side chains have been defined in the art. These families include amino acids with basic side chains (e.g. lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g. glycine, alanine, valine, leucine, isoleucine, proline, phenylalanine, methionine, tryptophan, histidine). The resulting peptide comprising the substitution should have similar characteristics or properties including size, hydrophobicity, etc., such that the overall functionally of the peptide does not significantly change. As the structure of IF bound to $B_{12}$ is known in the art, a skilled artisan would be able to determine amino acids essential to $B_{12}$ binding to ensure binding to $B_{12}$ or a $B_{12}$ conjugate.

(d) Pharmaceutical Composition

The present disclosure also provides pharmaceutical compositions. The pharmaceutical composition comprises a complex of intrinsic factor and a $B_{12}$ conjugate, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered enterally (oral, gastric, rectal administration) or parenterally in dosage unit formulations containing conventional nontoxic pharmaceutically acceptable carriers, adjuvants, and vehicles as desired. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980). In a specific embodiment, a composition may be an oral composition.

Dosage forms for enteral administration include pills, tablets, caplets and capsules (chewable, dissolvable or swallow), time-release and sustained-release tablets and capsules, powders of granules, pellets, teas, drops, liquid or syrups (solution, softgel, suspension, emulsion, elixir, tincture, hydrogel), film, lollipop, lozenges, chewing gum, and oral spray. In such dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

The compositions may be presented in unit-dose or multidose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

In certain embodiments, a composition comprising a complex of intrinsic factor and a $B_{12}$ conjugate is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a complex of intrinsic factor and a $B_{12}$ conjugate in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a complex of intrinsic factor and a $B_{12}$ conjugate may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidyletha- nolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a complex of intrinsic factor and a $B_{12}$ conjugate (i.e., having at least one methionine compound) may be prepared by any known method of preparing liposomes for drug delivery, such as, for example, detailed in U.S. Pat. Nos. 4,241,046, 4,394,448, 4,529,561, 4,755, 388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A complex of intrinsic factor and a $B_{12}$ conjugate may be encapsulated in a microemulsion by any method generally known in the art.

In yet another embodiment, a complex of intrinsic factor and a $B_{12}$ conjugate may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

In an aspect, a composition of the invention may be used in a method of protecting a peptide from protease degradation. The method comprises conjugating a peptide to a $B_{12}$, such that a $B_{12}$-peptide conjugate is formed; contacting the $B_{12}$-peptide conjugate with intrinsic factor, such that a complex comprising intrinsic factor and $B_{12}$-peptide conjugate is formed; and exposing the complex to a protease, wherein the peptide within the complex is protected from protease degradation relative to the peptide alone or the peptide conjugated to $B_{12}$.

In another aspect, a composition of the invention may be used in a method of protecting a peptide against protease degradation following oral administration to a subject. The method comprises conjugating a peptide to a $B_{12}$, such that a $B_{12}$-peptide conjugate is formed; contacting the $B_{12}$-peptide conjugate with intrinsic factor, such that a complex comprising intrinsic factor and $B_{12}$-peptide conjugate is formed; and administering a pharmaceutical composition comprising the complex to the subject, wherein the peptide within the complex is protected from protease degradation relative to the peptide alone or the peptide conjugated to $B_{12}$. In a specific embodiment, the composition may be administered orally.

In still another aspect, a composition of the invention may be used in a method of protecting a peptide against protease degradation following administration to a subject. The method comprises administering to the subject a pharmaceutical composition comprising intrinsic factor complexed with $B_{12}$ or analog thereof, wherein the $B_{12}$ or analog thereof is conjugated to a peptide and wherein the peptide within the complex is protected from protease degradation relative to the peptide alone or the peptide conjugated to $B_{12}$. In a specific embodiment, the composition may be administered orally.

By protecting from protease degradation is meant that more than 5% of the peptide is intact in the presence of proteases. Intact peptide may be measured by assessing peptide function using means commonly known in the art. For example, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 95%, or more than 99% of the peptide is intact in the presence of proteases. In certain embodiments, more than 10% of the peptide is intact in the presence of proteases. In other embodiments, more than 20% of the peptide is intact in the presence of proteases. In still other embodiments, more than 50% of the peptide is intact in the presence of proteases. In certain embodiments, 50% to 100% of the peptide is intact in the presence of proteases.

Using a method of the invention, a peptide within a complex is protected from protease degradation relative to a peptide alone or a peptide conjugated to $B_{12}$. Protection may be measure by peptide activity. Accordingly, a peptide within a complex may be at least 2-fold more active relative to a peptide alone or a peptide conjugated to $B_{12}$. For example, a peptide within a complex may be at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, at least 40-fold, at least 45-fold, or at least 50-fold more active relative to a peptide alone or a peptide conjugated to $B_{12}$. In certain embodiments a peptide within a complex may be at least 2-fold to at least 10-fold more active relative to a peptide alone or a peptide conjugated to $B_{12}$.

Peptide digestion from proteases in the gastrointestinal tract is a significant limitation in oral peptide therapeutic development. By avoiding peptide cleavage, bioavailability of the peptide may be enhanced. Thus, the methods disclosed herein provide a significant advantage over the prior art. The ability to protect the peptide from protease degradation potentially increases the bioavailability of the peptide by allowing its absorption via the IF-$B_{12}$ pathway prior to degradation and inactivity of the peptide. Accordingly, the bioavailability of the peptide conjugated to $B_{12}$ and complexed with IF may be increased relative to a peptide alone or a peptide conjugated to $B_{12}$.

A method of the invention may be used protect a peptide against protease degradation following administration to a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In certain embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

In some embodiments, if the method of the invention is used to protect a peptide against protease degradation following administration to a particular subject, the IF used in the complex is also derived from the same species as the subject. For instance, if the complex is administered to a human, human IF is used. If the complex is administered to a canine, then canine IF is used. It is contemplated, however, that in other embodiments, if the method of the invention is used to protect a peptide against protease degradation following administration to a particular subject, the IF used in the complex is derived from a different species than the subject.

Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

The frequency of dosing may be daily or multiple times per day or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Enhanced Peptide Stability Against Trypsin Digestion Induced by Intrinsic Factor Binding of a Vitamin $B_{12}$ Conjugate of Exendin-4

The human vitamin $B_{12}$ ($B_{12}$) dietary uptake pathway is a complex process that facilitates access in humans to a vital cofactor of methionine synthase and methyl malonyl CoA mutase enzymes. This pathway involves three major binders, two of which, Intrinsic Factor (IF) and Haptocorrin (HC), being critical for oral uptake (the third, Transcobalamin II (TCII) facilitates entry into cells upon enterocyte passage). HC primarily protects $B_{12}$ against acid digestion in the stomach, and is enzymatically digested upon entry of the HC-$B_{12}$ complex into the duodenum, whereupon the $B_{12}$ is bound by IF. While IF is produced in gastric parietal cells and can bind $B_{12}$ in the stomach, HC binding is preferred at the lower pH and it is only upon digestion of HC and a rise in pH in the intestine that IF binding of $B_{12}$ occurs naturally. Concomitant with the rise in pH is the release of pancreatic proteases and it is critical to note that IF, unlike HC, is resistant to pancreatic protease digestion. IF is critical then for delivery of $B_{12}$ through the intestinal tract to the ileum where cubilin-amnionless based receptor mediated enterocyte passage occurs. Employing this pathway for oral peptide delivery requires conjugation of the peptide to $B_{12}$ in such a way that IF recognition of $B_{12}$ is not critically hindered and that the $B_{12}$ conjugated peptide can still exhibit the desired pharmacological function.

An example of a peptide that could be orally delivered is Ex-4, which was discovered in the venom of the Gila monster in 1992 and is an incretin mimetic, sharing 53% homology with glucagon-like peptide-1 (GLP-1). Like GLP-1, Ex-4 stimulates the release of insulin through agonism of the GLP-1 receptor (GLP-1R) ($EC_{50}$ 33 pM), effectively lowering blood glucose levels. Unlike GLP-1, Ex-4 is resistant to the enzyme dipeptidyl peptidase IV (DPP-IV), which rapidly cleaves and inactivates GLP-1 in vivo. Since DPP-IV cleaves any peptide with an alanine or proline at the second position from the N-terminal, substituting a glycine for the alanine in GLP-1 results in the resistance seen in Ex-4. This resistance allows Ex-4 to have a half-life of 2.4 h compared to <2 min as seen for GLP-1. Such resistance to DPP-IV does not however translate to pancreatic proteases, so Exenatide must be administered subcutaneously to have the desired effect.

This pancreatic degradation limitation may also be overcome, at least to some degree above unmodified peptide, by conjugating $B_{12}$ to Ex-4 and subsequently adding IF, assuming the necessary maintenance of $B_{12}$ binding by IF, and Ex-4 agonism are controlled. The present invention was tested by synthesizing a $B_{12}$-Ex-4 conjugate focusing on the lysine 12 (K12) position of Ex-4 and the ribose 5'-hydroxyl group of the $B_{12}$ moiety as sites of conjugation, since both sites on the respective moieties had published precedent for allowable modification. Binding to IF was confirmed by radioassay and agonism of the GLP-1 receptor was then established for Ex-4, $B_{12}$-Ex-4 and IF-$B_{12}$-Ex-4. With such establishing parameters controlled for, stability against the proteases trypsin and chymotrypsin were compared for Ex-4, $B_{12}$-Ex-4 and IF-$B_{12}$-Ex-4.

(AzidoK12)-Ex-4, HGEGTFTSDLS(Kazido)QMEEE-AVRLFIENWLKNGGPSSGAPSSGAPPPS (SEQ. ID. NO: 1) (compound 1) was conjugated to $B_{12}$ at the K12 position using Huisgens/Sharpless click chemistry, using Ex-4 modified at the lysine 12 ε-amine with an azido group during solid-phase synthesis. The 5' hydroxyl group of $B_{12}$ was also modified prior to coupling, being selectively oxidized to a carboxylic acid (compound 2) using 2-iodoxybenzoic acid. As seen in FIG. 1, subsequent coupling of 1-amino-3-butyne to compound 2 with 1-Ethyl-3-(3-dimethylaminopropyl)carbodiimide (EDCl) and 1-Hydroxybenzo-triazole (HOBt) produced $B_{12}$ with a terminal alkyne at the ribose 5'-position (compound 3). Compound 3 was purified using a Shimadzu Prominence HPLC on an Eclipse XDB C18 5 μm 4.6 mm×150 mm column with a mobile phase of 0.1% TFA water and elution with acetonitrile on a gradient starting at 15% acetonitrile increasing to 35% over 20 minutes.

Figure 2:
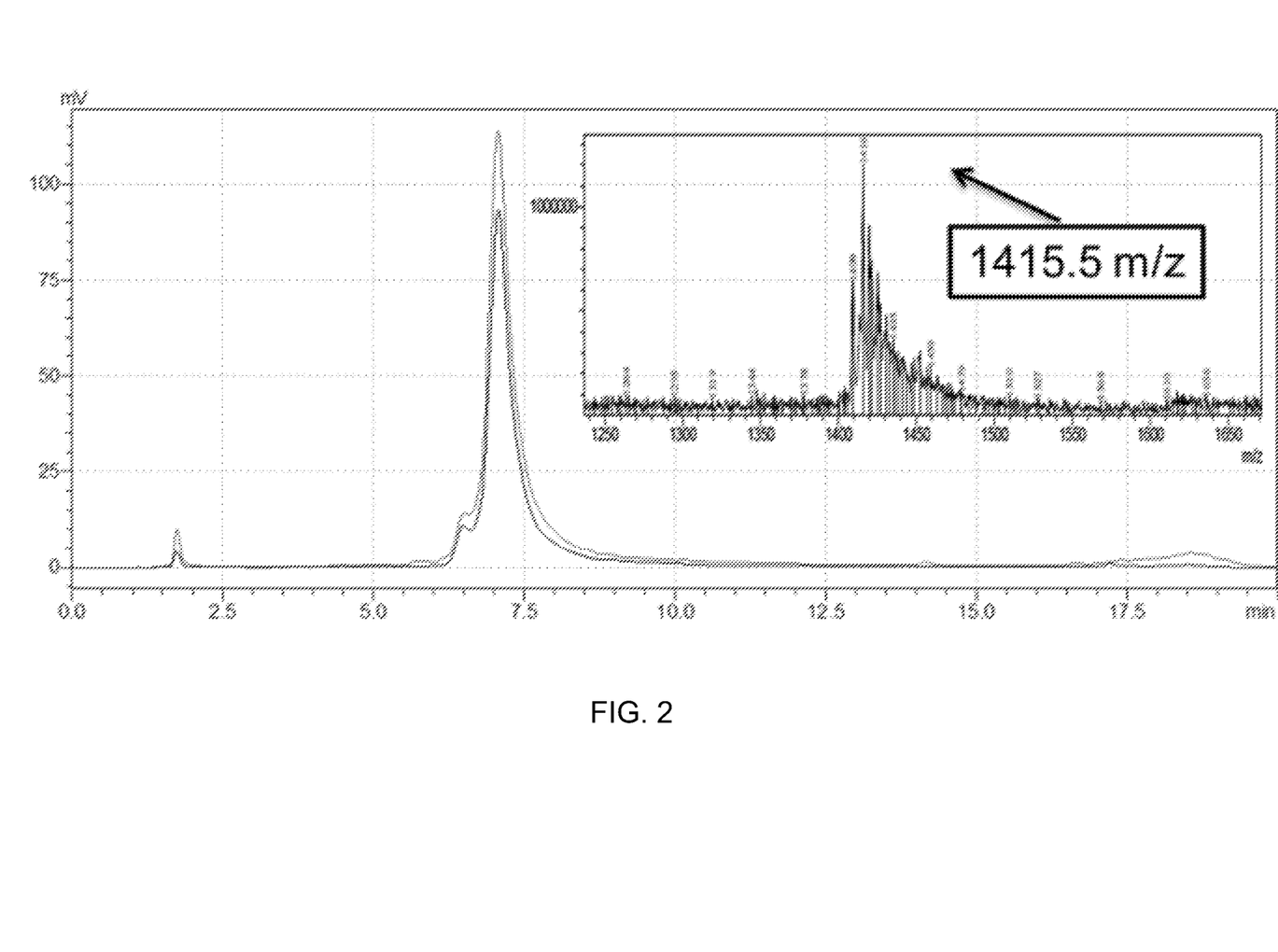
FIG. 2 depicts an LC trace showing purified 4 as a monomer (7.5 min) and dimer (6.5 min) and ESI MS (inset) of compound 4 showing m/z of 1415.5 Da, which corresponds to the +4 of 4 yielding a consistent mass of 5658 Da.

As further seen in FIG. 1, compounds 1 and 3 were coupled using copper (II) sulphate and sodium L-ascorbate. The new $B_{12}$-Ex-4 conjugate (compound 4) was purified with a Shimadzu HPLC using an Eclipse XDB C18 5 μm 4.6 mm×150 mm column with a mobile phase of 0.1% TFA water and elution with acetonitrile. A gradient run from 20% acetonitrile to 42% acetonitrile during the first three minutes and then 42 to 47.5% acetonitrile during the next ten minutes was used to separate 4 from starting materials. The product was confirmed by electrospray ionization mass spectrometry (ESI MS) as seen in FIG. 2. Compound 4 was purified to greater than 97% purity by HPLC as additionally seen in FIG. 2. The tendency of Ex-4 to aggregate resulted in a small shoulder at 6.5 minutes.

Figure 3:
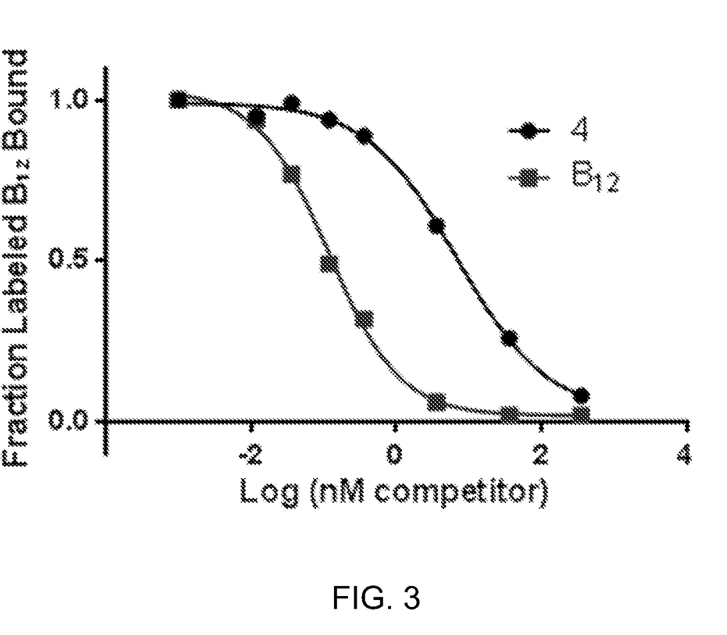
FIG. 3 depicts a graph showing IF binding to $B_{12}$ (0.12 nM) and compound 4 (6.8 nM). IF used in these assays was produced in the plant *Arabidopsis* in the apo-form and of high purity.

Initially, IF binding of compound 4 was confirmed by radiometric chase assay using $^{57}$Co-labelled $B_{12}$ and compared to free $B_{12}$, as cyanocobalamin, as seen in FIG. 3. Significant IF binding of 4 (6.8 nM) was maintained, albeit reduced from unmodified $B_{12}$ (0.12 nM).

Once IF binding of compound 4 (IF-4) was confirmed, agonism of the GLP-1R was assayed for compound 1, compound 4 and IF-4 using HEK-293 cells stably transfected with the GLP-1R (HEK-GLP-1R). To this end, a new assay was employed that uses adenoviral transduction to express the genetically-encoded FRET reporter AKAR3 that serves as a sensitive readout for cAMP production due to the fact that AKAR3 undergoes a decrease of 485/535 nm emission FRET ratio when it is phosphorylated by cAMP-dependent protein kinase (PKA) subsequent to GLP-1R activation. This is the first instance of a FRET assay for GLP-1R using viral AKAR3 and offers a ready route to sensitive high-throughput screening of the GLP-1R.

Figure 4:
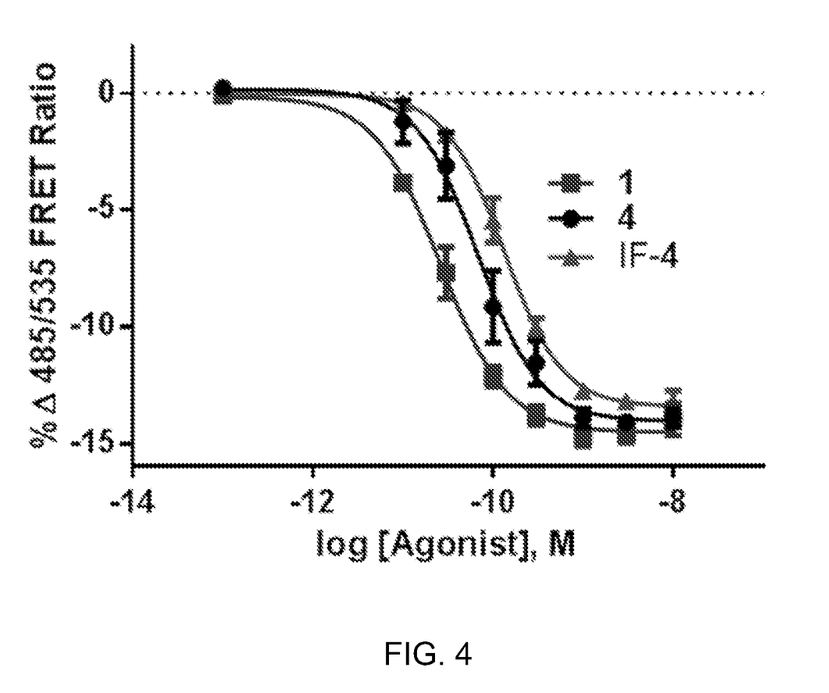
FIG. 4 depicts a graph of a dose-response analysis of compound 1, compound 4, and IF-compound 4. Compound 1, compound 4, and IF-compound 4 yielded $EC_{50}$ values of 26, 68, and 132 pM respectively, as determined by monitoring the 485/535 nm FRET emission ratio.

An $EC_{50}$ for compound 1, compound 4 and IF-4 were measured at 26 pM, 68 pM and 132 pM, respectively, as seen in FIG. 4. It is worth noting that the azido modification to the K12 position of Ex-4 showed no significant reduction in potency compared to unmodified Ex-4 suggesting a useful general route for selective conjugation to Ex-4 through click chemistry approaches. Compound 4 and IF-4 show that further conjugation to the K12 position effects functions but still demonstrates low picomolar effective concentrations.

Compound 1, compound 4 and IF-4 were analysed for stability against proteases by measuring remaining function at the receptor compared to undigested controls. Compound 1, compound 4 and IF-4 were tested for function at [100 nM], a concentration at which each had comparable percent change in FRET ratio, as seen in Table 1 below:

TABLE 1

% Change in FRET at 100 nM for 1, 4 and IF-4.

| Compound | % Change in FRET at 100 nM |
|---|---|
| 1 | −12 ± 0.01 |
| 4 | −13 ± 0.02 |
| IF-4 | −12 ± 0.01 |

Digestion was conducted in a standard extracellular solution containing either trypsin at 11, 22, or 50 μg/mL or chymotrypsin at 1.25, 3, or 6.25 μg/m L.

Figure 5:
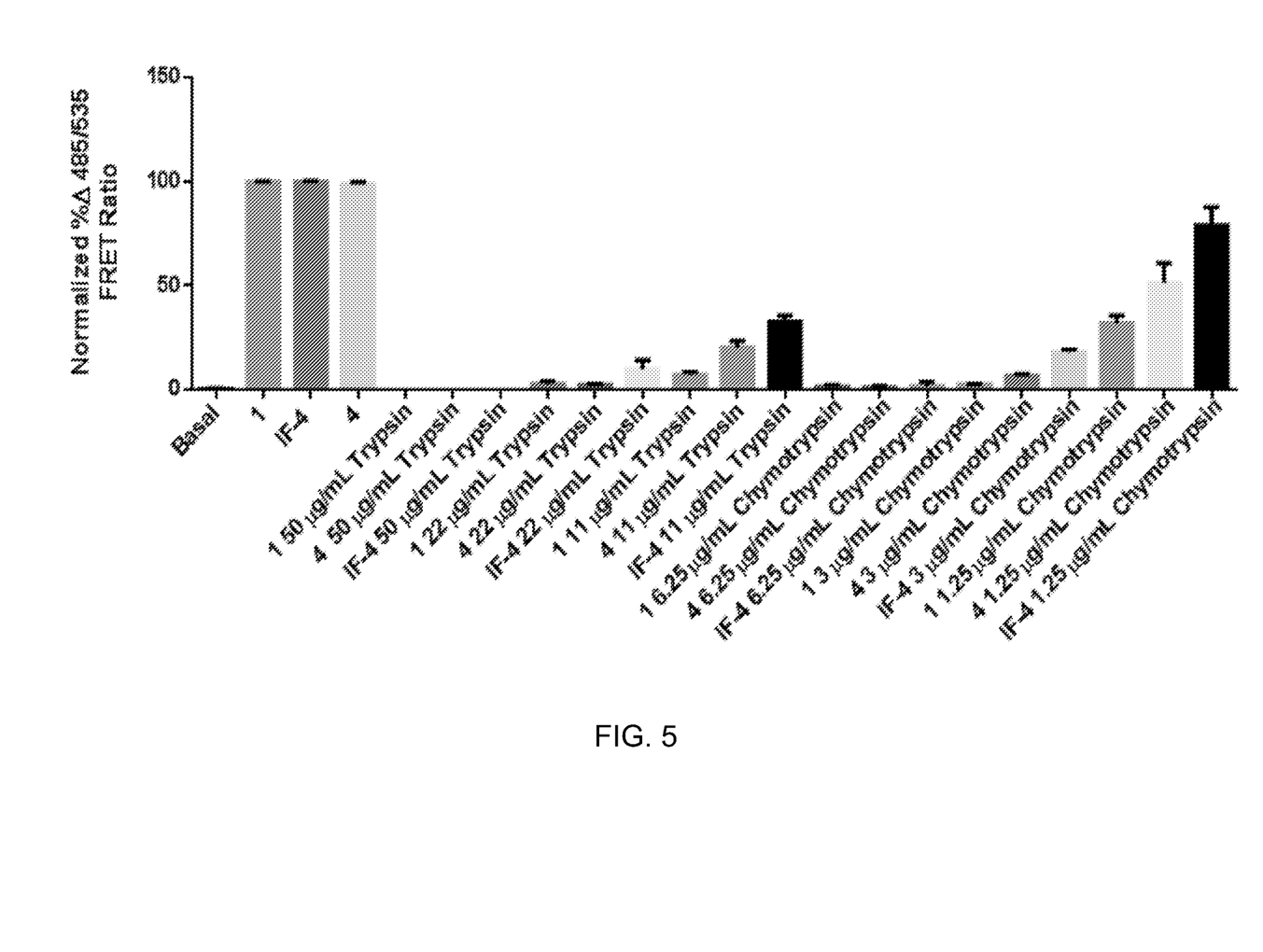
FIG. 5 depicts a chart of 1.5 h trypsin and chymotrypsin digestion of 100 nM compound 1, compound 4 and IF-compound 4 with 50, 22 or 11 µg/mL of trypsin or 1.25, 3, or 6.25 µg/mL of chymotrypsin using AKAR3 to measure function. The data shows the maximum expression normalized to 100% of the conjugates done in triplicate (mean±SEM) and basal control contained trypsin at 50 µg/mL of trypsin. (N.C.=no change).

Three concentrations of each protease were used to track the relative differences between compound 4 and IF-4. At the lowest concentration of trypsin (11 μg/mL) and chymotrypsin (1.25 μg/mL) there is up to 50% greater function for IF-4 relative to compound 4 alone with the highest concentration of trypsin (50 μg/mL) and chymotrypsin (6.25 μg/mL) assayed showing complete lack of function for all systems, as seen in FIG. 5. The digestion was monitored by measuring agonism of the drugs at the GLP-1R, initially over the course of 3 h, although it was quickly noted that there was no change after 1.5 h, indicating that the digestion had stopped by this time point (data not shown). Subsequent triplicate runs were then performed on digestions of 1.5 h.

Results of the AKAR3 assays show maintenance of function where otherwise none was observed or improvement of function when compound 4 is first bound to IF. $B_{12}$ conjugation itself offered some protection at low protease concentrations.

Figure 6:
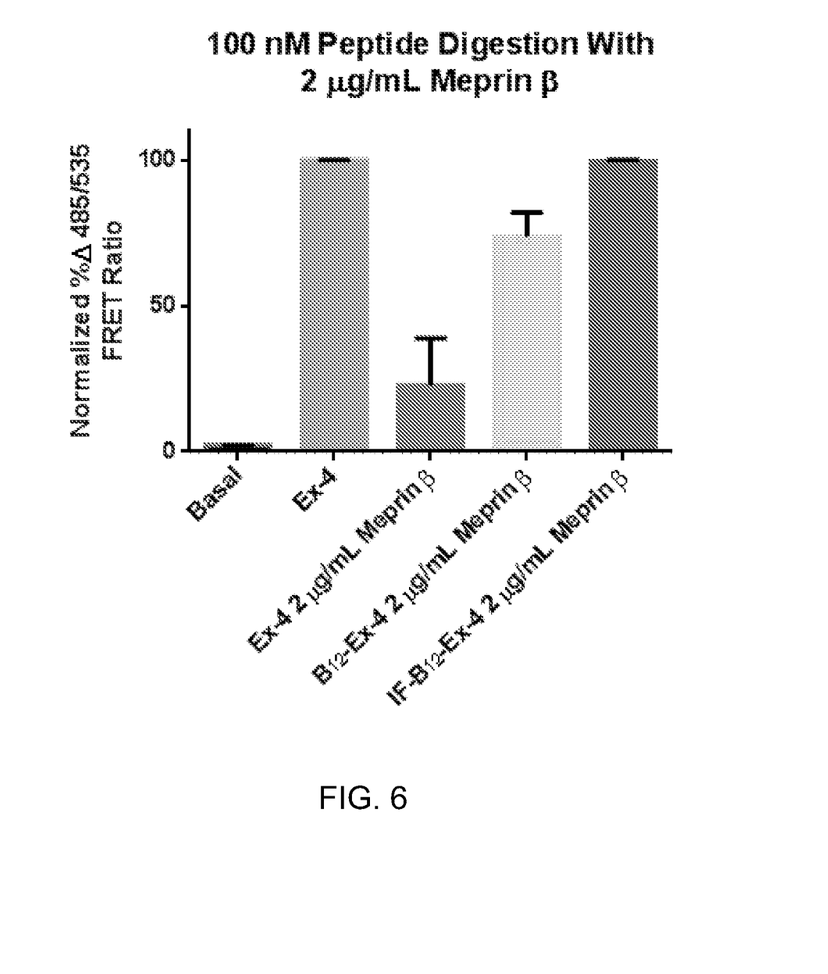
FIG. 6 depicts a chart of Meprin β digestion of 100 nM compound 1, compound 4 and IF-compound 4 with 2 µg/mL of Meprin β.
Figure 7:
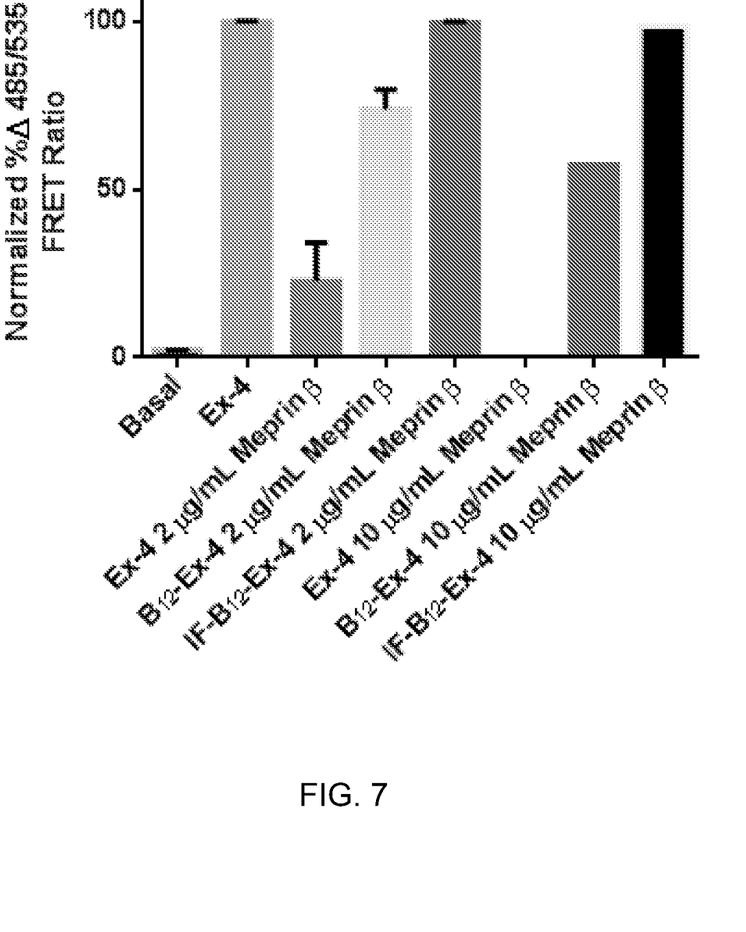
FIG. 7 depicts a chart of is a chart of Meprin β digestion of 100 nM compound 1, compound 4 and IF-compound 4 with 2 and 10 µg/mL of Meprin β. The data shows the maximum expression normalized to 100% of the conjugates done in triplicate (mean±SEM) and basal control contained Meprin β at 10 µg/mL of Meprin β.

As seen in FIG. 6 and FIG. 7, $B_{12}$ conjugation offered some protection against Meprin β protease and IF binding to the $B_{12}$ conjugate offered significant protection against the kidney protease, thus demonstrating efficacy against gastrointestinal and serum proteases. The use of $B_{12}$ and intrinsic factor thus provides a mechanism for protecting proteins against proteases, whether the protein is delivered orally or by intraperitoneal, subcutaneous, or intravenous injection.

The conservation or improved relative function demonstrated herein for Ex-4 when conjugated to $B_{12}$ and, more significantly, when bound by IF relates to the use of IF in delivering and protecting an orally administered peptide. Protection against pancreatic protease-catalysed hydrolytic digestion of compound 4 was maximal at an optimal trypsin concentration of 22 μg/mL of trypsin and 3 μg/mL of chymotrypsin when compound 4 was pre-bound to IF, providing a 4-fold and 7.5-fold positive increase in function respectively as measured by GLP-1R agonism (utilizing a new AKAR3 screening assay). $B_{12}$ provided some protection against trypsin relative to the native peptide. The effect is seen at 11 μg/mL of trypsin with a relative increase of 3-fold and at 1.25 and 3 μg/mL of chymotrypsin with a relative increase of 3 and 1.6-fold. The fact that the IF bound form IF-4 still maintained significant function at the GLP-1R is also highly significant since many routes to protect against intestinal degradation involve encapsulation, which prevents possible luminal function or absorption when in place. The use of IF to improve the protease stability of a peptide offers significant possibilities. Even a small improvement in oral function may be sufficient to achieve the targeted effect. Combining this approach with a highly potent peptide with known gut receptors that can produce a vagal afferent response (such as, but not limited to, GLP-1/Ex-4 or $PYY_{3-36}$ for example) and may allow for a positive clinical outcome to be achieved orally without need even for systemic delivery. Finally, there is no suggestion that this approach is limited to use against gastric proteases, but could also be expanded into serum proteases possibly facilitating improved pharmacokinetics for instance.

What is claimed is:

1. A method of protecting against protease degradation, comprising the steps of:
   a) forming a conjugate of a peptide and a molecule of $B_{12}$, wherein the peptide comprises the sequence set forth in SEQ ID NO:1 or SEQ ID NO:2; and
   b) binding intrinsic factor to the conjugate of the peptide and the molecule of B12.

2. The method of claim 1, wherein the steps of forming a conjugate of a peptide and the molecule of $B_{12}$ and binding intrinsic factor to the conjugate of the peptide and the molecule of $B_{12}$ are performed prior to administering the peptide to a patient.

3. The method of claim 2, wherein the peptide is conjugated to a 5' hydroxyl group of the molecule of $B_{12}$ that has been oxidized to a carboxylic acid.

4. The method of claim 3, further comprising the step of orally administering the conjugate of the peptide and the molecule of $B_{12}$ that is bound to intrinsic factor to a subject.

5. A method of protecting a peptide against protease degradation, the method comprising:
   a) conjugating a peptide to a $B_{12}$, wherein the peptide comprises the sequence set forth in SEQ ID NO:1 or SEQ ID NO:2, such that a $B_{12}$-peptide conjugate is formed;
   b) contacting the $B_{12}$-peptide conjugate with intrinsic factor, such that a complex comprising intrinsic factor and $B_{12}$-peptide conjugate is formed; and
   c) exposing the complex to a protease, wherein the peptide within the complex is protected from protease degradation relative to the peptide alone or the peptide conjugated to B12.

6. A method of protecting a peptide against protease degradation following administration to a subject, the method comprising:
   a) conjugating a peptide to a $B_{12}$, wherein the peptide comprises the sequence set forth in SEQ ID NO:1 or SEQ ID NO:2, such that a $B_{12}$-peptide conjugate is formed;
   b) contacting the B12-peptide conjugate with a pharmaceutically acceptable intrinsic factor, such that a complex comprising intrinsic factor and $B_{12}$-peptide is formed,
   c) administering a pharmaceutical composition comprising the complex to the subject, wherein the peptide within the complex is protected from protease degradation relative to the peptide alone or the peptide conjugated to $B_{12}$.

7. A method of protecting a peptide against protease degradation following administration to a subject, the method comprising administering to the subject a pharmaceutical composition comprising intrinsic factor complexed with $B_{12}$ or analog thereof, wherein the $B_{12}$ or analog thereof is conjugated to a peptide and wherein the peptide comprises the sequence set forth in SEQ ID NO:1 or SEQ ID NO:2 and is protected from protease degradation relative to the peptide alone or the peptide conjugated to $B_{12}$.

8. The method of claim 7, wherein the bioavailability of the peptide within the complex is increased relative to the peptide alone or the peptide conjugated to $B_{12}$.

9. The method of claim 7, wherein the IF is purified from *Arabidopsis*.

10. The method of claim 7, wherein the peptide is conjugated to $B_{12}$ at the 5'-hydroxyl of the ribose.

11. The method of claim 10, wherein the 5'-hydroxyl of the ribose is oxidized to a carboxylic acid prior to conjugation to the peptide.

12. The method of claim 7, wherein the peptide is EX-4.

13. The method of claim 7, wherein the peptide comprises the sequence set forth in SEQ ID NO:1 or SEQ ID NO:2.

14. The method of claim 13, wherein the peptide comprising SEQ ID NO:1 is conjugated to the 5'-hydroxyl group of the ribose of $B_{12}$ via the azido group at lysine 12 of the peptide.

15. The method of claim 7, wherein the proteases are pancreatic proteases.

16. The method of claim 7, wherein the pharmaceutical composition is administered orally.

* * * * *

SEQUENCE LISTING

<160> NUMBER OF SEQ ID NOS: 2

<210> SEQ ID NO 1
<211> LENGTH: 45
<212> TYPE: PRT
<213> ORGANISM: Artificial Sequence
<220> FEATURE:
<223> OTHER INFORMATION: exendin-4 based peptide from Heloderma
      suspectum modified with azido

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Asn Trp Leu Lys Asn Gly Gly Pro
            20                  25                  30

Ser Ser Gly Ala Pro Ser Ser Gly Ala Pro Pro Pro Ser
        35                  40                  45

```
<210> SEQ ID NO 2
<211> LENGTH: 45
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Asn Trp Leu Lys Asn Gly Gly Pro
            20                  25                  30

Ser Ser Gly Ala Pro Ser Ser Gly Ala Pro Pro Pro Ser
        35                  40                  45
```